United States Patent [19]

Sherlock et al.

[11] 4,127,112
[45] Nov. 28, 1978

[54] SKIN FOLD CALIPER

[75] Inventors: Hugh P. Sherlock, Palo Alto; Allan M. Golderg, Laguna Niguel; Werner W. Ciupke, Burlingame; George Brody, San Clemente, all of Calif.

[73] Assignee: American Hospital Supply Corp., Evanston, Ill.

[21] Appl. No.: 785,130

[22] Filed: Apr. 6, 1977

[51] Int. Cl.² .............................................. A61B 5/10
[52] U.S. Cl. .................................. 128/2 S; 33/143 C; 128/321
[58] Field of Search ................ 128/2 S, 361, 321–325; 33/143 C, 174 D, 148 C, 148 F

[56] References Cited

U.S. PATENT DOCUMENTS

| 2,472,126 | 6/1949 | Robinson | 33/164 R |
| 3,140,546 | 7/1964 | Bartlett | 33/148 F |
| 3,906,957 | 9/1975 | Weston | 128/321 |
| 3,921,640 | 11/1975 | Freeborn | 128/321 X |

FOREIGN PATENT DOCUMENTS

| 212,976 | 5/1967 | Sweden | 33/143 C |
| 1,330,985 | 9/1973 | United Kingdom | 33/143 C |

OTHER PUBLICATIONS

The Lancet, Oct. 29, 1960, p. 962.

*Primary Examiner*—Kyle L. Howell
*Attorney, Agent, or Firm*—Y. Judd Azulay

[57] ABSTRACT

Skin Fold Caliper having first and second relatively rigid arms which have one end of each of the first and second members connected to permit pivotal movement of the first and second arms with respect to each other so that the other ends of the first and second arms can be moved between open and closed positions. A gauge is carried by the first and second arms for giving an indication of the spacing between the other ends of the first and second arms. A spring-like member formed integral with one of the arms is utilized for applying a predetermined clamping pressure between the first and second arms to move the other ends of the first and second arms toward the closed position.

8 Claims, 3 Drawing Figures

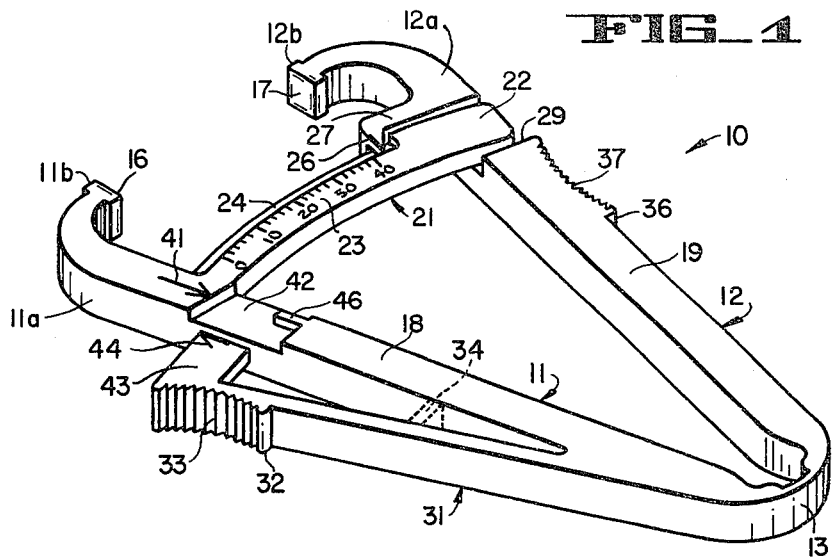
FIG_1
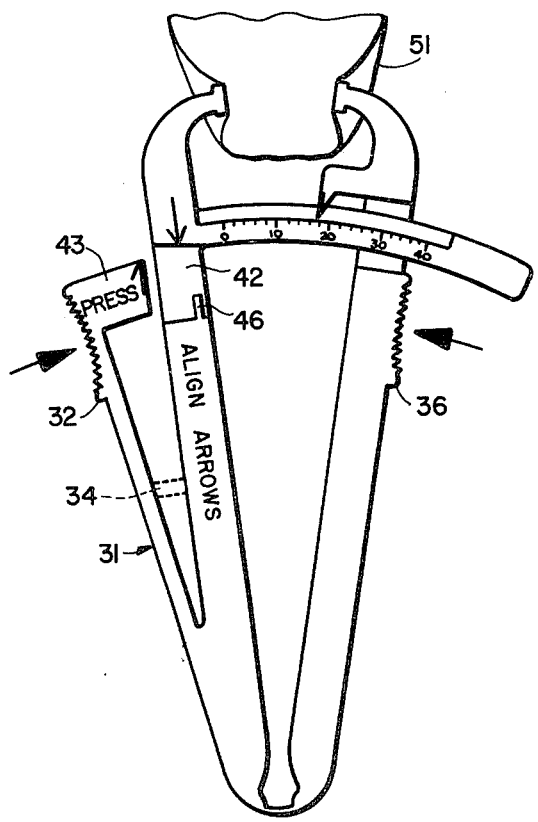
FIG_2
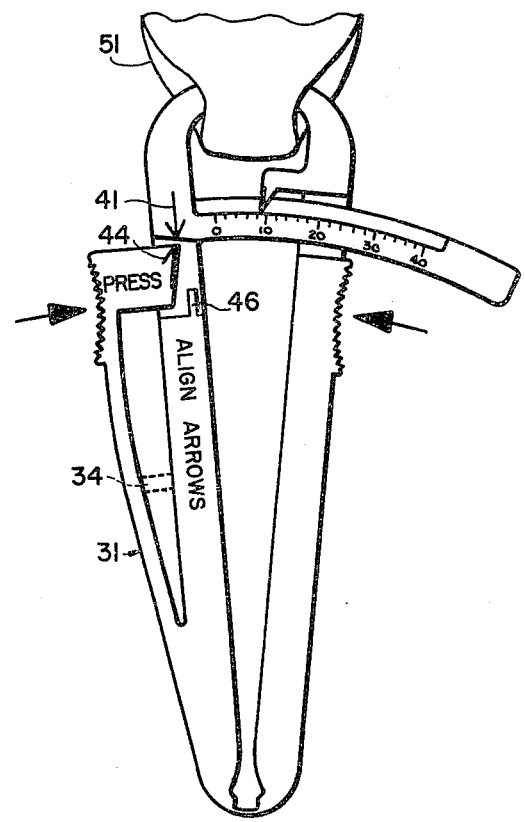
FIG_3

SKIN FOLD CALIPER

BACKGROUND OF THE INVENTION

Skin Fold Calipers have heretofore been provided for measuring fat content. However, in the past such Skin Fold Calipers in general have been rather complicated and very expensive. Therefore there is a need for a new and improved Skin Fold Caliper which is low in cost.

OBJECTS AND SUMMARY OF THE INVENTION

The Skin Fold Caliper consists of first and second relatively rigid arms. Means is provided interconnecting one end of each of the first and second arms for permitting pivotal movement of the first and second arms with respect to each other so that the other ends of said first and second arms can be moved between open and closed positions. Means is carried by the first and second arms for yieldably urging the first and second arms towards the open position. Cooperative guage means is carried by the first and second arms for giving an indication of the spacing between the other ends of the first and second arms. Means is carried by one of the arms at an angle with respect to said one arm for applying a predetermined clamping force between said first and second arms to move the first and second arms towards the closed position.

In general it is an object of the invention to provide a skin fold caliper which is low in cost.

Another object of the invention is to provide a caliper of the above character which is formed in one piece.

Another object of the invention is to provide a caliper of the above character which is formed from plastic.

Another object of the invention is to provide a caliper of the above character which can be used on skin folds of various sicknesses. Another object of the invention is to provide a caliper of the above character in which the inherent springness of the plastic is utilized to apply a yieldable force between the arms.

Another object of the invention is to provide a caliper of the above character which can be molded into one piece without use of any cross slides in the mold.

Another object of the invention is to provide a caliper of the above character which can be snapped together after it has been formed.

Additional objects and features of the invention will appear from the following description in which the preferred embodiment has been set forth in detail in connection with the accompanying drawings.

BRIEF DESCRIPTION OF THE DRAWINGS

FIG. 1 is an isometric view of a skin fold caliper incorporating the present invention.

FIGS. 2 and 3 are cross sectional views showing the manner in which the caliper is utilized for measuring the skin fold and how a predetermined pressure is applied during the measurment.

DESCRIPTION OF THE PREFERRED EMBODIMENT

The skin fold caliper incorporating the present invention is shown in FIGS. 1, 2, and 3 of the drawings and consists of first and second relatively rigid arms 11 and 12. Means is provided for interconnecting one end of each of the first and second arms for permitting pivotal movement of the first and second arms with respect to each other so that the other ends of the first and second arms can be moved between open and closed positions. In order to simplify the construction of skin fold caliper and to make it a one-piece construction as hereinafter described, this means takes the form of a relatively thin interconnecting spring member 13. This spring member 13 is formed integral with the arms 11 and 12. In order that the member 13 have the desired characteristics, the arms 11 and 12 and the member 13 are formed of a suitable plastic, such as acetal. If desired, the arms 11 and 12 can be formed solid or in order to conserve material, they can be formed so that they are generally U-shaped in cross section with the channel (not shown) extending longitudinally of the same. The outer ends of the arms 11 and 12 are provided with inwardly curved portions 11a and 12a respectively. The outer extremities of the corners portions 11a and 12a are provided with enlarged portions 11b and 12b. These enlarged portions 11b and 12b are provided with faces 16 and 17 respectively which extend generally running parallel to the outer extremities of the curved portions 11a and 12a and as shown generally face each other in the spaced apart positions. The arms 11 and 12 are provided with a surfaces 18 and 19 respectively which lie generally in the same plane.

Cooperative gauge means is carried by the first and second arms and gives an indication of the spacing between the faces 16 and 17 of the outer or other ends of the arms 11 and 12. As shown in FIGS. 1, 2, and 3, the cooperative gauge means consists of an arcuate gage member 21 formed integral with the arm 11 and being adjacent to the outer end of the arm 11 but being spaced from the outer curved portion 11a of the arm 11. The gauge member 21 extends approximately at right angles to the surface 18 of the arm 11. The gauge member 21 is provided with a radius of coverature of a circle considering the spring member 13 forming the center of the circle. The gauge member 21 is provided with a surface 22 which is provided with indicia 23 calibrated from 0 to 40 millimeters extending from the face 16 to the face 17. The gauge member 21 is provided with an accurate recess 24 about the upper or outer extremity of the same which is adapted to receive a pointer 26. The pointer 26 is carried by a protrusion 27 formed integral with the arm 12. As can be seen in FIG. 1, the gauge member 21 extends through a slot 29 formed in the member 12 and extending through the surface 19. It can be seen that the recess 24 is longer then the 40 millimeter dimension and that the engagement of the pointer 26 with the end of the recess 24 is to provide a stop to eliminate the outward movement of the outer ends of the arms 11 and 12 with respect to each other to determine the open position for the arms 11 and 12.

Means is carried by the first and second arms formed integral with one of the arms for applying a predetermined clamping force between the face 16 and 17 carried by the first and second arms 11 and 12 to move the outer ends of the arms 11 and 12 toward the closed position. This means consists of a spring-like member 31 which has one end secured to the arm 11 adjacent to the portion of the arm 11 which is in a relative close proximity to the spring member 13. The spring member 31 is in the form of an elongate lever arm which is inclined at an outward angle with respect to the arm 11. The outer extremity of the member 31 is provided with a curved finger grip 32 having a serrations 33 formed therein. In order to provide the desired spring force as hereinafter described, it may be necessary as shown in FIG. 1 to provide a reinforcing bar or strut 34 (shown in broken lines) which may be formed integral with the member 31 and the arm 11 to shorten the lever arm provided by the spring-like member 31. A corresponding finger grip 36 is provided on the outer surface of the arm 12 which also has serrations 37 therein.

Cooperative gauge means is carried by the spring-like member 31 by the arm 11 for determining when a predetermined clamping force is being applied between the faces 16 and 17 at the outer ends of the arms 11 and 12. This means consists of the arrow 41 which is carried by the arm 11 in close proximity to a slot 42 formed in the arm 11 adjacent to the region at which the gauge member 21 is secured to the arm 11. The arrow 41 can be formed in the member 11 in a suitable manner such as by embossing the same into the member 11. A flag 43 is formed on the outer end of the spring-like member 31 and is positioned in such a manner that it is adapted to move into the slot 42 provided in the member 11. An arrow 44 is formed on the flag 43 in a suitable manner such as by embossing the same into the flag 43. A stop 46 is formed in the slot 42 and is positioned in such a manner so that it is adapted to be engaged by the flag 43 to prevent movement of the flag 43 and the outer extremity of the spring-like member 31 beyond a predetermined position. As shown the stop 46 is formed integral with the arm 11.

From the construction hereinbefore described, it can be seen that the skin fold caliper is formed in one piece. The caliper has been designed in such a manner that it can be formed in a mold without any use of cross slides in the mold. In formation of the caliper, the gauge member 21 is free of the pointer 26 so that the outer extremity of the member 21 is not disposed in the slot 29. After the skin fold caliper has been molded and removed from the mold, the gauge member 21 can be readily inserted into the slot 29 by slightly depressing the same below the pointer 26. Since the skin fold caliper is formed of a spring-like plastic, namely acetal as hereinbefore described, the deflection can be readily accomplished. As soon as the gauge member 21 is released, the pointer 26 will snap into the recess 24 and will retain the gauge member 21 within the slot 29.

It should be appreciated that the skin fold caliper can be designed for various clamping forces. By way of example, the present skin fold caliper has been designed when arrows 41 and 44 are in alignment to provide a clamping force of 0.4 lbs. plus or minus 0.04 of a pound.

Operation and use of the skin fold caliper can now be readily described as follows: The skin fold caliper can be readily grasped by the hand depending upon which hand is utilized for cooperating the skin fold caliper. The thumb and the forefinger can be utilized for gripping the opposite finger grips 32 and 36. A fold of skin 51 taken in a suitable part of the human body is clamped between the faces 16 and 17 of the skin fold caliper as shown in FIG. 2. Pressure is applied to the finger grips 32 and 36 to cause deformation of the spring-like member 31 shown in FIG. 3 until the arrows 41 and 44 are brought into alignment with each other as shown in FIG. 3. This indicates that a predetermined clamping pressure as for example the 0.4 lbs. hereinbefore described is being applied to the skin fold 51. As soon as the arrows are in alignment, a reading then can be made on the scale 23 of the thickness of the skin fold which will give an indication of the fat content in a manner well known to those skilled in the art. As soon as this reading has been accomplished, the force being applied to the finger grips 32 and 36 can be released to release the skin fold 51. Another skin fold measurement can be made on another part of the same human body to make another reading. This procedure can be continued until the desired number of thickness readings have been obtained.

It should be appreciated that as soon as the finger grips 32 and 36 are released, the force provided by the spring number 13 is sufficient to urge the arms 11 and 12 to their outer most positions so that the pointer 26 engages the outer extremeity of the recess 24. The spring-like member 31 will also move to its outermost position as shown in FIG. 1. The stop member 46 prevents an operator from pressing the outer extemity of the spring-like member 31 beyond a predetermined position and possibly breaking the same.

It can be appreciated from the foregoing construction that there has been provided a skin fold caliper that which is relatively simple in construction and particularly one that can be formed in one piece from plastic. This makes it possible to reduce the cost to such an extent that it can be considered as a give-away item or at most a item which can be sold relatively inexpensively. The skin fold caliper has been designed in such a manner that it can be readily used with a minimum of instruction. Relatively simple instructions are provided on the skin fold caliper its self which makes the operation of the device apparent to one attempting to utilize the same. As pointed out previously, the construction is such that it can be formed in one piece in molds without the use of cross slides in the mold. It also can be appreciated that the spring-like member 31 can be designed in such a manner so that different clamping forces can be provided if desired. It can be readily increased by the addition of the strut.

We claim:

1. In a skin fold caliper:
    first and second relatively rigid arms, means connecting one end of each of the first and second arms with respect to each other so that the other ends of said first and second arms can be moved between open and closed positions,
    cooperative gauge means carried by said first and second arms for giving an indication of the spacing between the other ends of said first and second arms,
    means carried by said first and second arms,
    a spring-like member associated with said last named means,
    said spring-like member having one end secured to one of said arms and having the other end free,
    a cooperative gauge means carried by said spring-like member and said one arm,
    registration arrows carried by said spring-like member and said one arm, and
    the arrow carried by said spring-like member is carried by a flag and said one arm is provided with a slot adapted to receive said flag.

2. The caliper of claim 1 wherein said means carried by said first and second arms is formed integral with one of said arms for applying a predetermined clamping force between the other ends of said arms to move the other ends of said first and second arms towards the closed position.

3. The caliper of claim 1 wherein said spring-like member is positioned so that it can be engaged by one finger of a hand while another finger of the same hand can be utilized to engage the other arm to apply the predetermined clamping force between the other ends of said first and second arms.

4. The caliper as in claim 1 wherein said cooperative gauge means carried by said spring-like member and said one arm comprises means for determining when said predetermined clamping force is being applied between said other ends of said first and second arms.

5. A caliper as in claim 1 together with means carried by the first and second arms for yieldably urging said first and second arms towards said open position.

6. A caliper as in claim 1 together with stop means carried by said one arm for preventing deflection of said spring-like member beyond a predetermined amount.

7. A caliper as in claim 1 wherein said cooperative gauge means carried by said first and second arms for indicating the spacing between the other ends of said first and second arms includes an arcuate member carried by one of said arms, the other of said arms having a slot formed therein and adapted to receive the arcuate gauge member and means carried by the other of said arms and said arcuate gauge member for limiting movement of said other arm with respect to said gauge member.

8. A caliper as in claim 7 wherein said gauge member is provided with a recess extending longitudinally thereof and a pointer carried by said other arm extending into said recess.

* * * * *

UNITED STATES PATENT OFFICE
CERTIFICATE OF CORRECTION

Patent No. 4,127,112           Dated November 28, 1978

Inventor(s) Hugh P. Sherlock, et al

It is certified that error appears in the above-identified patent and that said Letters Patent are hereby corrected as shown below:

On the title page, the inventor "Allan M. Golderg" should be deleted to insert --Allan M. Goldberg--.

Signed and Sealed this

Twentieth Day of March 1979

[SEAL]

Attest:

RUTH C. MASON
*Attesting Officer*

DONALD W. BANNER
*Commissioner of Patents and Trademarks*